United States Patent
Nielsen et al.

(10) Patent No.: US 8,384,379 B2
(45) Date of Patent: Feb. 26, 2013

(54) NON-DESTRUCTIVE DETERMINATION OF THE PORE SIZE DISTRIBUTION AND THE DISTRIBUTION OF FLUID FLOW VELOCITIES

(75) Inventors: Robert D. Nielsen, Lambertville, NJ (US); Hans Thomann, Bedminster, NJ (US)

(73) Assignee: ExxonMobil Upstream Research Company, Houston, TX (US)

(\*) Notice: Subject to any disclaimer, the term of this patent is extended or adjusted under 35 U.S.C. 154(b) by 319 days.

(21) Appl. No.: 12/675,087

(22) PCT Filed: Oct. 1, 2008

(86) PCT No.: PCT/US2008/078482
§ 371 (c)(1),
(2), (4) Date: Feb. 24, 2010

(87) PCT Pub. No.: WO2009/048781
PCT Pub. Date: Apr. 16, 2009

(65) Prior Publication Data
US 2011/0095757 A1 Apr. 28, 2011

Related U.S. Application Data

(60) Provisional application No. 60/998,717, filed on Oct. 12, 2007.

(51) Int. Cl.
*G01V 3/00* (2006.01)
*G01V 33/20* (2006.01)
(52) U.S. Cl. ........ 324/303; 324/306; 324/307; 324/318; 367/73; 73/152.18
(58) Field of Classification Search .......... 324/300–322; 382/128–133; 600/407–464
See application file for complete search history.

(56) References Cited

U.S. PATENT DOCUMENTS
4,291,271 A 9/1981 Lauffer
(Continued)

FOREIGN PATENT DOCUMENTS
EP 0 581 666 2/1994
GB 2 310 724 3/1997
(Continued)

OTHER PUBLICATIONS

Appel, M. (2004), "Nuclear Magnetic Resonance and Formation Porosity", Petrophysics V 45, No. 3, pp. 296-307, May-Jun. (ISSN 15299074).

(Continued)

*Primary Examiner* — Melissa Koval
*Assistant Examiner* — Emily Chan
(74) *Attorney, Agent, or Firm* — ExxonMobil Upstream Research Company Law Dept.

(57) ABSTRACT

A method is disclosed for the non-destructive determination of the pore size distribution and the distribution of fluid flow velocities using NMR spin echo signal measurements. In one embodiment, the invention involves simultaneously injecting acoustic energy (208), generating a magnetic field having a gradient, and injecting radio-frequency electromagnetic energy (206) into a subsurface region, using for example an NMR tool and a well logging tool having an acoustic transmitter placed in a wellbore (202). The spin echo signal generated in the subsurface region is measured (210) by the NMR tool for at least two values (212) of the magnetic field gradient. A relationship is provided by which the pore fluid velocity distribution may be calculated (214) from the inverse Fourier transform of the spin echo data. The pore size distribution may then be calculated from the pore fluid velocity distribution.

29 Claims, 7 Drawing Sheets

U.S. PATENT DOCUMENTS

| | | | | |
|---|---|---|---|---|
| 4,719,423 | A | * | 1/1988 | Vinegar et al. .............. 324/303 |
| 4,781,460 | A | | 11/1988 | Bott |
| 5,428,291 | A | * | 6/1995 | Thomann et al. .............. 324/303 |
| 5,698,979 | A | | 12/1997 | Taicher et al. |
| 5,712,566 | A | | 1/1998 | Taicher et al. |
| 5,757,186 | A | | 5/1998 | Taicher et al. |
| 5,828,214 | A | | 10/1998 | Taicher et al. |
| 5,834,936 | A | | 11/1998 | Taicher et al. |
| 6,018,243 | A | | 1/2000 | Taicher et al. |
| 6,069,477 | A | | 5/2000 | Chen et al. |
| 6,084,408 | A | | 7/2000 | Chen et al. |
| 6,118,272 | A | | 9/2000 | Taicher et al. |
| 6,121,773 | A | | 9/2000 | Taicher et al. |
| 6,140,818 | A | | 10/2000 | Hurlimann |
| 6,204,663 | B1 | | 3/2001 | Prammer |
| 6,246,236 | B1 | | 6/2001 | Poitzsch et al. |
| 6,268,726 | B1 | | 7/2001 | Prammer et al. |
| 6,346,813 | B1 | | 2/2002 | Kleinberg |
| 6,362,619 | B2 | | 3/2002 | Prammer et al. |
| 6,452,388 | B1 | | 9/2002 | Reiderman et al. |
| 6,470,274 | B1 | | 10/2002 | Mollison et al. |
| 6,478,096 | B1 | | 11/2002 | Jones et al. |
| 6,493,632 | B1 | | 12/2002 | Mollison et al. |
| 6,518,758 | B1 | | 2/2003 | Speier et al. |
| 6,528,995 | B1 | | 3/2003 | Speier et al. |
| 6,529,833 | B2 | | 3/2003 | Fanini et al. |
| 6,531,869 | B1 | | 3/2003 | Speier et al. |
| 6,538,438 | B1 | | 3/2003 | Speier et al. |
| 6,568,487 | B2 | | 5/2003 | Meister et al. |
| 6,570,381 | B1 | | 5/2003 | Speier et al. |
| 6,583,621 | B2 | | 6/2003 | Prammer et al. |
| 6,600,316 | B2 | | 7/2003 | Chen et al. |
| 6,603,310 | B2 | | 8/2003 | Georgi et al. |
| 6,609,568 | B2 | | 8/2003 | Krueger et al. |
| 6,618,322 | B1 | | 9/2003 | Georgi |
| 6,640,908 | B2 | | 11/2003 | Jones et al. |
| 6,642,715 | B2 | | 11/2003 | Speier et al. |
| 6,686,736 | B2 | | 2/2004 | Schoen et al. |
| 6,710,596 | B2 | | 3/2004 | Speier et al. |
| 6,720,765 | B2 | | 4/2004 | Edwards et al. |
| 6,755,246 | B2 | | 6/2004 | Chen et al. |
| 6,825,659 | B2 | | 11/2004 | Prammer et al. |
| 6,833,698 | B2 | | 12/2004 | Sun et al. |
| 6,844,727 | B2 | | 1/2005 | Kruspe et al. |
| 6,856,132 | B2 | | 2/2005 | Appel et al. |
| 6,871,713 | B2 | | 3/2005 | Meister et al. |
| 6,897,651 | B2 | | 5/2005 | Reidermann et al. |
| 6,897,652 | B2 | | 5/2005 | Appel et al. |
| 6,933,719 | B2 | | 8/2005 | Thomann et al. |
| 7,011,155 | B2 | | 3/2006 | Meister et al. |
| 7,012,426 | B2 | | 3/2006 | Edwards et al. |
| 7,032,661 | B2 | | 4/2006 | Georgi et al. |
| 7,053,611 | B2 | | 5/2006 | Freedman |
| 7,084,625 | B2 | | 8/2006 | Kruspe et al. |
| 7,116,103 | B2 | | 10/2006 | Edwards et al. |
| 7,126,333 | B2 | | 10/2006 | Beard et al. |
| 7,157,915 | B2 | | 1/2007 | Schoen et al. |
| 7,180,288 | B2 | | 2/2007 | Scheven |
| 7,196,516 | B2 | | 3/2007 | Blanz et al. |
| 7,199,580 | B2 | | 4/2007 | Akkurt |
| 7,227,355 | B2 | | 6/2007 | Chen et al. |
| 7,295,005 | B2 | | 11/2007 | Edwards |
| 7,298,142 | B2 | * | 11/2007 | Hursan et al. .............. 324/303 |
| 7,317,991 | B2 | | 1/2008 | Wang et al. |
| 7,388,373 | B2 | | 6/2008 | Lenormand et al. |
| 7,395,703 | B2 | | 7/2008 | Niemeyer et al. |
| 7,486,070 | B2 | | 2/2009 | Madio et al. |
| 7,501,817 | B1 | | 3/2009 | Luong et al. |
| 7,894,300 | B2 | * | 2/2011 | Hawthorn et al. .............. 367/73 |
| 2002/0175682 | A1 | | 11/2002 | Chen et al. |
| 2003/0214287 | A1 | * | 11/2003 | Sun et al. .............. 324/303 |
| 2004/0257241 | A1 | | 12/2004 | Menger |
| 2005/0007109 | A1 | * | 1/2005 | Thomann et al. .............. 324/303 |
| 2006/0071661 | A1 | | 4/2006 | Ong |
| 2008/0143330 | A1 | * | 6/2008 | Madio et al. .............. 324/303 |

FOREIGN PATENT DOCUMENTS

| | | |
|---|---|---|
| GB | 2 352 819 | 2/2001 |
| WO | WO 03/040743 | 5/2003 |

OTHER PUBLICATIONS

Bear, J. (1972), "The Equation of Motion of a Homogeneous Fluid", Dynamics of Fluids in Porous Media, American Elsevier Pub. Co., p. 163.

Coussot, P. et al. (2004), "Rheological Behavior of Drilling Muds, Characterization Using MRI Visualization", Oil and Gas Science and Technology—Rev. IFP, vol. 59, No. 1 pp. 23-29.

Drevs, J. et al. (2002),"PTK787/ZK 222584, A Specific Vascular Endothelial Growth Factor-Receptor Tyrosine Kinase Inhibitor, Affects the Anatomy of the Tumor Vascular Bed and the Functional Vascular Properties as Detected by Dynamic Enhanced Magnetic Resonance Imaging", Cancer Research 62, pp. 4015-4022.

Furrer, G. et al (1992), "The formation of polynuclear $Al_{13}$ under simulated natural conditions", Geochimica et Cosmochimica Acta, vol. 56, pp. 3831-3838.

Looyestijn, W.J. et al. (2006), "Permeability determination through NMR detection of acoustically induced fluid oscillation", Magnetic Resonance Imaging 24, pp. 1187-11201.

Moraczewski, T. (2005), "Flow of a concentrated suspension through an abrupt axisymmetric expansion measured by nuclear magnetic resonance imaging", Journal of Rheology, vol. 49, No. 6, pp. 1409-1428.

Parra, J .et al. (2002), "A Methodology to Integrate Magnetic Resonance and Acoustic Measurements for Reservoir Characterization: Annual Report (Apr. 2000-Apr. 2001)", US DOE Fossil Energy Report No. DOE/BC/15203-3 (OSTI ID: 790861), 103 pgs.

Parra, J. et al. (2003), "A Double-Porosity Poroelastic Model to Relate P-Wave (Pressure Wave) Attenuation to Fluid Flow in Vuggy Carbonate Rock", Royal Inst Technol. Coupled T-H-M-C Process in Geo-Systems: Fundamental, Modelling Exper. & Appl. (Geoproc. 2003) Int. Conf. (Stockholm, Sweden, Oct. 13-15, 2003) Proc Pt 1, pp. 481-486.

Polturak, E. et al. (1995), "NMR, optical, and plastic flow experiments in $bcc^3 He$—$^4$ He mixture crystals—in pursuit of a vacancy fluid", Journal of Low Temperature Physics, vol. 101, Nos. ½, pp. 177-183.

Sederman, J., et al. (2001), "Magnetic resonance visualisation of single- and two-phase flow in porous media", Magnetic Resonance Imaging, vol. 19, Issue 3, pp. 339-343.

Thomann, H. et al. (2006), "Fluid Flow Properties From Acoustically Stimulated Magnetic Field Gradient NMR", SPWLA 47th Annual Logging Symposium, Jun. 4-7, 2006, 6 pgs.

Uchikoshi, M. et al. (2003), "Fundamental study of the relation between flow velocity and signal intensity in the TruFISP sequence", Japanese Journal of Radiological Technology, vol. 59, No. 12, pp. 1529-1534, ISSN: 0369-4305.

Wahl, A. et al. (2004), "Capillary electrochromatography with polymeric continuous beds synthesized via free radical polymerization in aqueous media using derivatized cyclodextrins as solubilizing agents", Journal of Chromatography, 1044, pp. 211-222.

Zhang, X. et al. (2005), "Magnetic Resonance Microimaging and Numerical Simulations of Velocity Fields Inside Enlarged Flow Cells Used for Coupled NMR Microseparations" Anal Chem. 77, pp. 1338-1344.

*EP Search Report* dated Aug. 27, 2008 (Application No. 08003559.5-1240) Corresponding to PCT/US2008/78482.

*International Search Report* dated Dec. 5, 2008; PCT Application No. PCT/US2008/78482.

* cited by examiner

NON-DESTRUCTIVE DETERMINATION OF THE PORE SIZE DISTRIBUTION AND THE DISTRIBUTION OF FLUID FLOW VELOCITIES

CROSS-REFERENCE TO RELATED APPLICATION

This application is the National Stage of International Application No. PCT/US2008/078482, filed Oct. 1, 2008, which claims the benefit of U.S. Provisional Application No. 60/998,717, Oct. 12, 2007.

BACKGROUND

One of the major objectives of open hole logging in hydrocarbon exploration wells is to evaluate the fluid and fluid flow properties of the reservoir. Properties of particular interest include the relative fluid saturation at a given capillary pressure, the fluid flow permeabilities, and the fluid viscosities. These fluid flow properties are required to assess the economics of the reserve and for field development planning, such as the number of wells, well spacing, surface facilities, pipeline facilities, etc, which will be needed for production.

At present, these reservoir fluid flow parameters are determined using a variety of different approaches, including well flow testing, formation micro-test, coring and core analysis, and inference from continuous wireline well logging measurements. Each method is a trade-off between the cost of the measurement and the accuracy and associated uncertainties in the data and analysis. One of the advantages of continuous wireline logging is that it provides continuous data over the large reservoir intervals at much lower cost. The major disadvantage of current wireline logging measurements is that the fluid flow properties of the reservoir rock are inferred from measurements on non-flowing fluids, rather than measured directly on fluid flowing in the rock.

The fluid flow permeability, $\kappa$, is defined by Darcy's law:

$$v = -(\kappa/\eta)\nabla P$$

where $v$ is the flow velocity, $\nabla P$ is the pressure gradient and $\kappa/\eta$, is the ratio of permeability to viscosity. The latter is also known as the fluid mobility. Typically, the direct measurement of permeability is obtained by laboratory core analysis. In these laboratory measurements, the viscosity of the fluid and pressure gradient are known and the velocity is measured. The permeability is then readily derived from data fitting using the Darcy law definition of permeability.

SUMMARY

In one general aspect, a method of determining material properties within a portion of a fluid containing porous medium includes a) injecting acoustic energy into the portion of the porous medium; b) generating a magnetic field gradient within the portion of the porous medium; and c) injecting a radio frequency energy into the portion of the porous medium. The acoustic energy, the magnetic field gradient, and radio frequency energy have a predetermined relationship in time. The method further includes d) measuring an NMR signal from the portion of the porous medium; e) repeating a), b), c), and d) for one or more different values of the magnetic field gradient; and f) processing the measured NMR signals to determine one or more of the material properties of the portion of the porous medium.

Implementations of this aspect may include one or more of the following features. For example, the porous medium may be a sample selected from a portion of a subterranean formation, e.g., and the method is conducted in a laboratory setting. The porous medium is a portion of a subterranean formation, e.g., and a), b), and/or c) of the aforementioned method are conducted within the formation, e.g., with a downhole logging tool. Accordingly, a), b), and c) may be performed with a logging tool positioned within a wellbore of the portion of the subterranean formation. The remaining d), f), and/or g) may be performed downhole with the logging tool, through a system which includes processing the data downhole, or at least on location, and/or off-site, e.g., at a data processing facility.

The measured NMR signal detected may include a spin echo. The magnetic field gradient may be variable. The magnetic field gradient may vary with time. The magnetic field gradient may vary with spatial location. The magnetic field gradient may vary as a function of the desired resolution of the material properties. The material property may include one or more properties selected from the group consisting of fluid displacement, fluid velocity, a pore fluid velocity distribution, and/or an average pore fluid velocity, and/or any combination thereof. A relative pore size distribution may be determined from the pore fluid velocity distribution. An absolute pore size distribution may be determined from the pore fluid velocity distribution and the mean pore size. A Fourier inversion may be performed on the measured NMR signal to determine one or more of the material properties of the formation. A partial Fourier inversion may be performed on the measured NMR signal to determine one or more of the material properties of the formation. The statistical moments of the measured NMR signals may be determined to determine one or more of the material properties of the formation. The cumulants of the measured NMR signals may be determined to determine one or more of the material properties of the formation. The statistical moments from the measured NMR signal may be determined, and the correlations among the moments used in determining one or more of the material properties of the formation.

The acoustic energy may include a periodic acoustic signal. The periodic acoustic signal may include a plurality of operating phases and frequencies. The magnetic field gradient may include a plurality of operating frequencies. The radio frequency energy may include a plurality of operating phases and frequencies. A direction of the magnetic field gradient may be substantially the same as a direction of propagation of the acoustic energy. The spatial direction of the magnetic field gradient may not be the same as the direction of the propagating wave of the acoustic energy.

In another general aspect, a method of obtaining measurements that are representative of one or more material properties within a portion of a subterranean formation includes a) injecting acoustic energy into the portion of the formation; b) generating a magnetic field gradient within the portion of the formation; and c) injecting a radio frequency energy into the portion of the formation. The acoustic energy, the magnetic field gradient, and radio frequency energy have a predetermined relationship in time. The method includes d) measuring an NMR signal from the portion of the formation; and e) repeating a), b), c), and d) for one or more different values of the magnetic field gradient.

Implementations of this aspect may include one or more of the following features. The material properties may include a pore fluid velocity distribution. Accordingly, a), b), c), d) and e) may be performed on-site, e.g., with a downhole logging tool and a data acquisition system on-site, such as a surface facility nearby the downhole logging tool. In addition, the NMR signals may be processed on site or off-site.

For example, in another general aspect, a method of determining material properties within a portion of a subterranean formation includes processing NMR signals to determine one or more of the material properties of the portion of the subterranean formation. The NMR signals may have been acquired from a discrete location from where the NMR signals are later processed. However, the NMR signals were measured by a process which includes a) injecting acoustic energy into the portion of the formation; b) generating a magnetic field gradient within the portion of the formation; c) injecting a radio frequency energy into the portion of the formation. The acoustic energy, the magnetic field gradient, and radio frequency energy have a predetermined relationship in time. The process further includes d) measuring an NMR signal from the portion of the formation; and e) repeating a), b), c), and d) for one or more different values of the magnetic field gradient.

Implementations of this aspect may include one or more of the following features. For example, the material properties may include a pore fluid velocity distribution. Processing NMR signals to determine one or more of the material properties of the portion of the subterranean formation may include performing a Fourier inversion or partial Fourier inversion on the measured NMR signal to determine one or more of the material properties of the formation. Processing NMR signals to determine one or more of the material properties of the portion of the subterranean formation may include determining the statistical moments of the measured NMR signals to determine one or more of the material properties of the formation. Processing NMR signals to determine one or more of the material properties of the portion of the subterranean formation may include determining the cumulants of the measured NMR signals to determine one or more of the material properties of the formation. Processing NMR signals to determine one or more of the material properties of the portion of the subterranean formation may include determining the statistical moments from the measured NMR signal, and using the correlations among the moments in determining one or more of the material properties of the formation.

In another general aspect, a method of producing hydrocarbons from a subterranean formation includes a) injecting acoustic energy into the portion of the formation;
b) generating a magnetic field gradient within the portion of the formation; c) injecting a radio frequency energy into the portion of the formation. The acoustic energy, the magnetic field gradient, and radio frequency energy have a predetermined relationship in time. The method may include d) measuring an NMR signal from the portion of the formation; e) repeating a), b), c), and d) for one or more different values of the magnetic field gradient; f) processing the measured NMR signals to determine one or more of the material properties of the subterranean formation; and g) producing hydrocarbons from the subterranean formation as a function of the determined material properties of the formation.

Implementations of this aspect may include one or more of the following features. For example, the material properties comprise may include a pore fluid velocity distribution. The method may further include performing a Fourier inversion or partial Fourier inversion on the measured NMR signal to determine one or more of the material properties of the formation. The method may further include determining the statistical moments of the measured NMR signals to determine one or more of the material properties of the formation. The method may further include determining the cumulants of the measured NMR signals to determine one or more of the material properties of the formation. The method may further include determining the statistical moments from the measured NMR signal; and using the correlations among the moments in determining one or more of the material properties of the formation.

Implementations of one or more of any of the aforementioned aspects described hereinabove, may include one or more of the following features. For example, the predetermined relationship in time is that the acoustic energy, the magnetic field gradient, and radio frequency energy occur simultaneously at each measurement location. The material properties include fluid flow properties, and the fluid flow properties may be used to assess the economics of the subterranean formation or for planning development of hydrocarbon production from the subterranean formation.

In one embodiment, the porous medium is envisioned as, but not restricted to, a portion of a subterranean formation. Material properties include pore fluid velocity distribution and pore size distribution, from which many other petrophysical properties of the rock are derived. In one embodiment, the pore fluid velocity distribution is determined by performing an inverse Fourier transform of measured NMR spin echo signals. One or more embodiments may include materials measurements in a laboratory setting, such as rock core analysis. For example, the fluid containing porous medium may include a sample of a fluid containing porous medium selected from a portion of a subterranean formation for testing in a laboratory setting.

DETAILED DESCRIPTION

In wire line logging measurements, permeabilities are derived using empirical correlations established from laboratory measurements of permeability on cores and the characteristic tool response parameters. The primary tools used for this type of analysis are the sonic, electrical conductivity, and nuclear magnetic resonance (NMR) logging tools. For the sonic measurements, the permeability is derived from the attenuation of the elastic wave propagating along the borehole or in the formation. A major complication is that the attenuation is determined by the bulk properties, which includes both the grain and fluid properties. For the conductivity measurements, the permeability is derived using the Kozeny-Carmen relationship. A major complication in this measurement is that the conductivity varies with salinity as well as the relative saturation of hydrocarbons and also depends on the amount and types of clays and minerals present. Current NMR measurements employ a sequence of radio frequency pulses that generate the observable NMR signal, a spin echo. As the spacing of the radio frequency pulses increases, the resulting spin echo signal is attenuated with a characteristic relaxation time. From these NMR spin echo measurements, the permeability is inferred from an assumed simple relation between the distribution of NMR relaxation times and the pore size distribution. However this relationship is complex and the NMR relaxation time spectrum can only be converted to a pore size distribution in ideal circumstances when all relevant parameters such as the surface relaxivity and contributions of the pore-to-pore coupling are known. As a result of the complications in the interpretation of each of these measurements, the inferred permeability can have large uncertainties.

Figure 1:
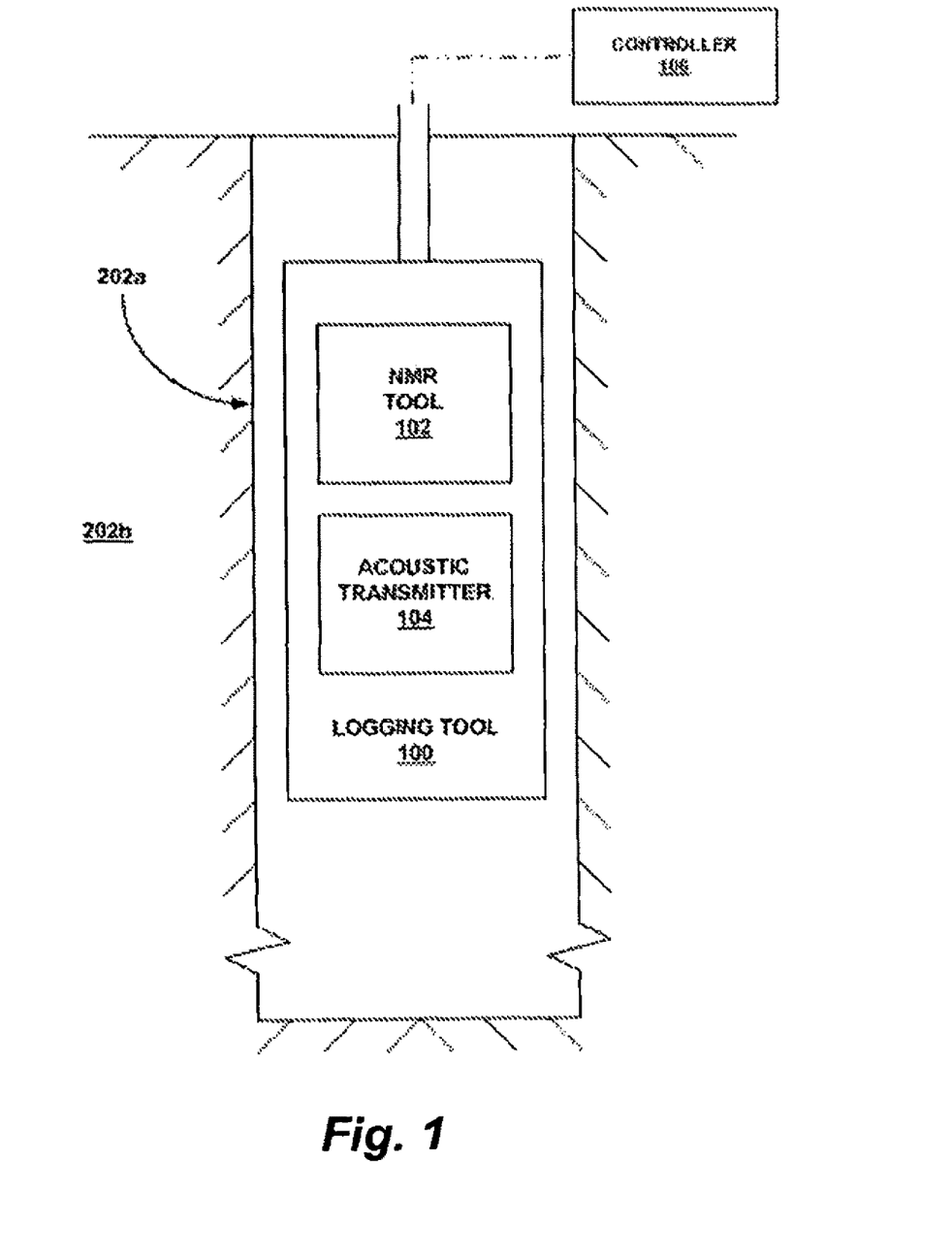
FIG. 1 illustrates a fragmentary cross-sectional illustration of an exemplary embodiment of a logging tool positioned within a wellbore that traverses a subterranean formation.

Referring initially to FIG. 1, an exemplary embodiment of a logging tool 100 includes a conventional nuclear magnetic resonance ("NMR") tool 102 and a conventional acoustic transmitter 104. A controller 106 is operably coupled to the NMR tool 102 and acoustic transmitter 104 for monitoring and controlling the operation of the NMR tool and the acoustic transmitter. The controller 106 may, for example, be a programmable general purpose computer.

Figure 2:
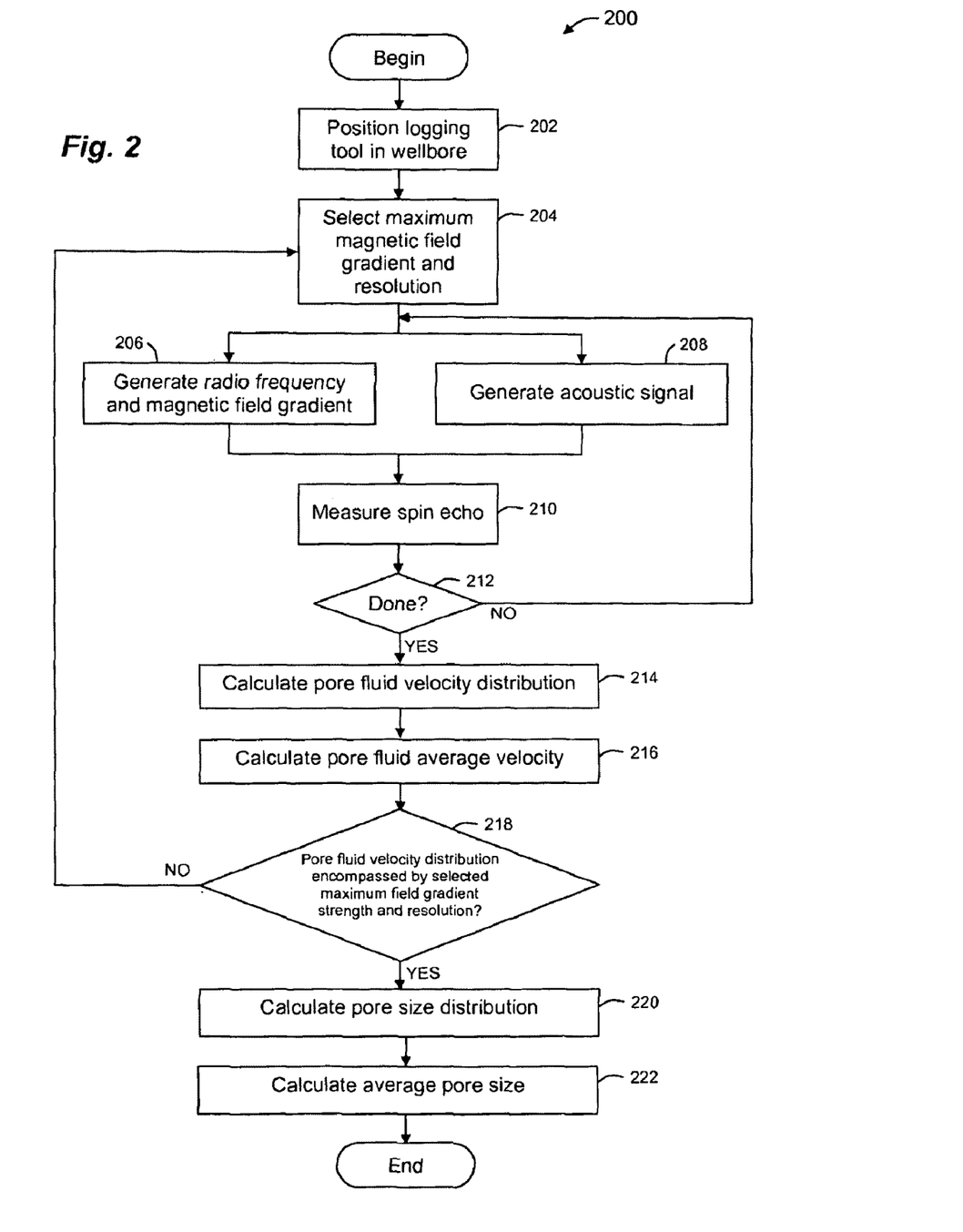
FIG. 2 is a flow chart representations of an exemplary embodiment of a method for determining the pore fluid velocity distribution, pore fluid average velocity, pore size distribution, and average pore size.

Referring to FIGS. 1 and 2, in an exemplary embodiment, the logging tool 100 is operated by implementing a method 200 for determining material properties in which, in 202, the logging tool 100 is positioned within a wellbore 202a that traverses a subterranean formation 202b.

In 204, the maximum gradient and resolution of the magnetic field generated by the NMR tool 102 of the logging tool 100 is then selected.

Figure 3A:
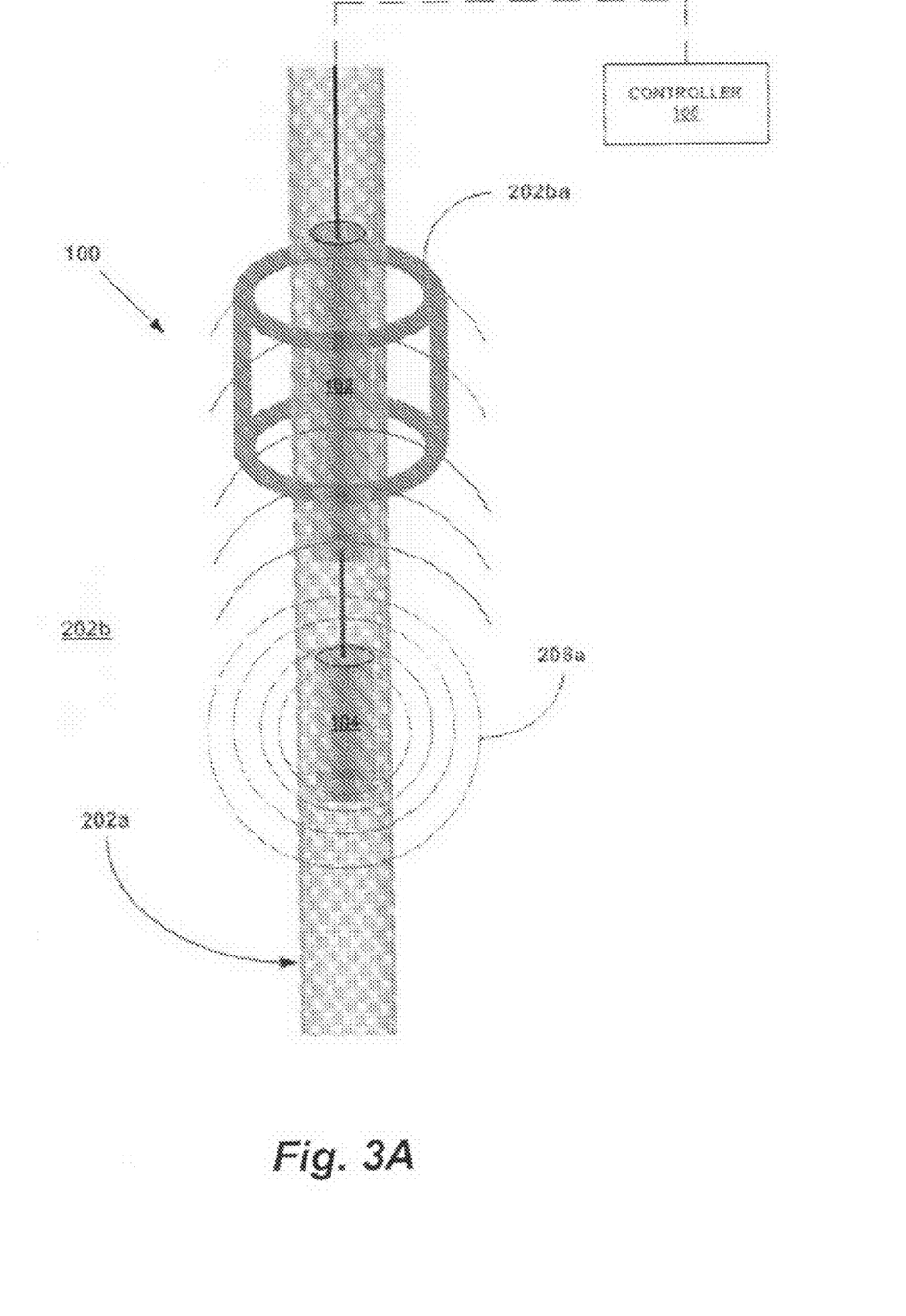
FIG. 3A illustrates an exemplary embodiment of the operation of the logging tool of FIG. 1.
Figure 3B:
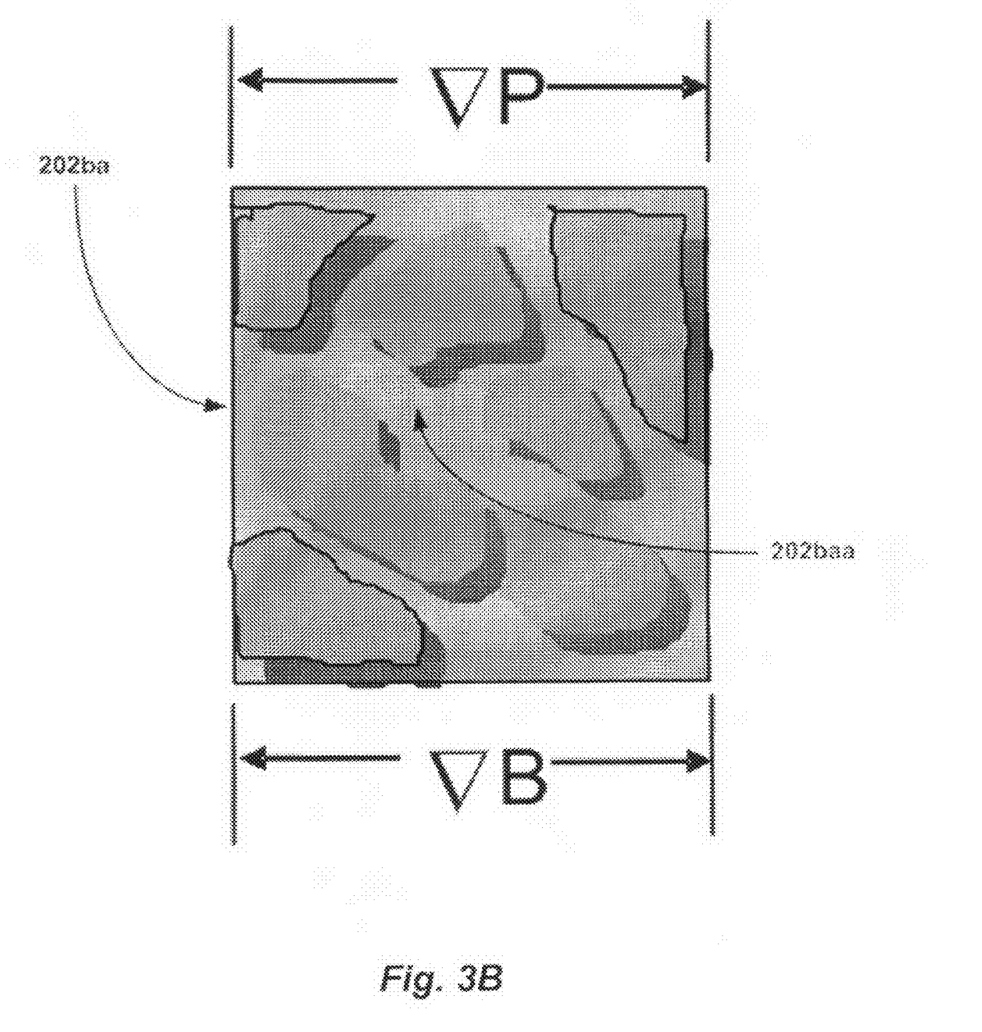
FIG. 3B illustrates an exemplary embodiment of a portion of the surrounding formation during the operation of the logging tool of FIG. 1.

In 206, as illustrated in FIG. 3A, the NMR tool 201 of the logging tool 100 is operated to generate and transmit a radio frequency signal into, and generate a magnetic field within, a volume 202ba within the formation 202b. In 208, the acoustic transmitter 104 of the logging tool is operated to generate and inject acoustic energy 208a into the volume 202ba of the formation 202b. In an exemplary embodiment, as illustrated in FIG. 3B, the volume 202ba defines one or more pores 206aa containing fluidic materials and operation of the logging tool 100 creates a pressure gradient ΔP and a magnetic field gradient ΔB within the volume.

In 210, the NMR tool 102 of the logging tool 100 monitors and records the NMR signal generated within the volume 202ba of the formation 202b.

In an exemplary embodiment, 206, 208 and 210 are repeated until a complete set of data is collected in 212.

In an exemplary embodiment, 206, 208 and 210 are repeated for different values of the magnetic field gradient.

In an exemplary embodiment, 206, 208 and 210 are repeated for different values of the temporal relationship between the radio frequency and acoustic stimuli. For example, the timing of the NMR radio frequency pulses may be adjusted relative to the phase of a periodic acoustic stimulus.

In an exemplary embodiment, 206, 208, and 210 are repeated using measurements of the spin echo from different physical locations within the formation 202b by, for example, varying the frequency of the RF signal in 206.

Figure 3C:
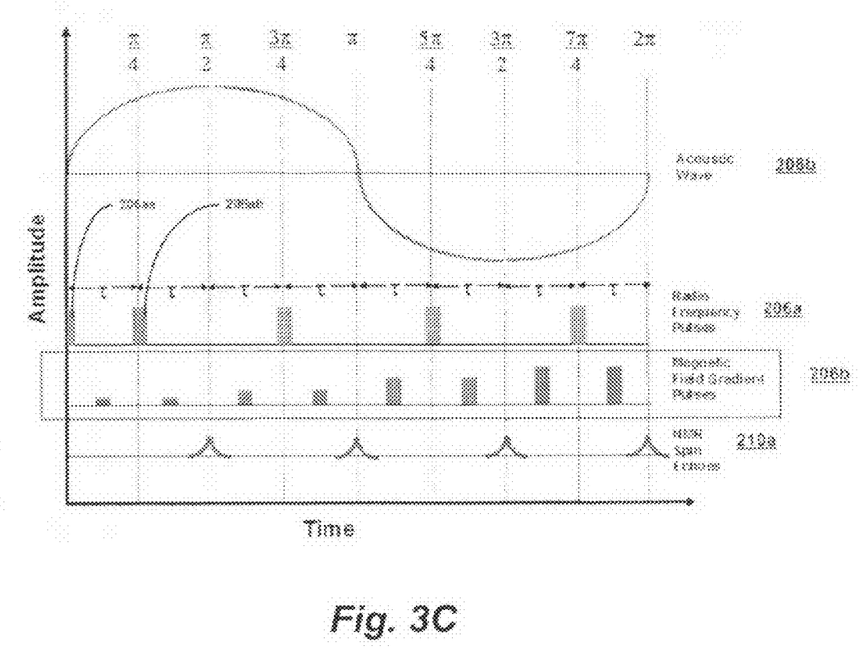
FIG. 3C is a graphical timing diagram illustrating and exemplary embodiment of the operation of the logging tool of FIG. 1.

In an exemplary embodiment, as illustrated in FIG. 3C, in 206, the NMR tool 102 of the logging tool 100 is operated to transmit radio frequency pulses in the form of a Carr-Purcell-Meiborn-Gill pulse sequence and magnetic field gradient pulses, 206a and 206b, respectively, into the volume 202ba of the formation 202b. In an exemplary embodiment, the initial radio frequency pulse 206aa is spaced from the next radio frequency pulses 206ab by a time period τ and the next radio frequency pulses are spaced apart by a time period equal to 2τ. In an exemplary embodiment, the magnitudes of pairs of the magnetic field gradient pulses 206b are the same before and after corresponding next radio frequency pulses 206ab. In an exemplary embodiment, each subsequent pair of magnetic field gradient pulses 206b are of increased magnitude from the prior pair of magnetic field gradient pulses.

In an exemplary embodiment, in 208, the acoustic transmitter 104 of the logging tool 100 is operated to generate and inject an acoustic wave 208b into the volume 202ba of the formation 202b. In an exemplary embodiment in 210, the NMR tool 102 of the logging tool 100 is operated to monitor and record MNR spin echoes 210a generated by the Carr-Purcell-Meiborn-Gill pulse sequence within the volume 202ba by the operation of the logging tool.

In an exemplary embodiment, in 214, the data collected in 206, 208 and 210 is then processed to calculate the pore fluid velocity distribution.

In particular, in an exemplary embodiment, in 214, the data collected in 206, 208, and 210 is then processed to calculate the pore fluid velocity distribution function $P(\vec{v})$ within the volume 202ba:

$$P(\vec{v}) = \frac{1}{2\pi|\vec{\chi}|} \int_{-\infty}^{\infty} e^{i\gamma \vec{G} \cdot \vec{\chi} \cdot \vec{v}} \hat{P}_{NMR}(\gamma \vec{G} \cdot \vec{\chi}) d\vec{G} \cdot \vec{\chi} \tag{1}$$

The theoretical basis for the relationship in equation (1) above is as follows.

The acoustic component of the position of a fluid element within the volume 202ba may be specified by a three dimensional vector $\vec{R}(\vec{v}, \omega_a, t)$, where $\vec{v}$ is the pore fluid velocity vector, $\omega_a$ is the acoustic driving frequency of the acoustic transmitter 104 of the logging tool 100, and t is time. The dependence of the fluid response on $\omega_a$ will be taken as arbitrary, and can be construed as a zero frequency constant pressure gradient or as a set of frequencies. A set of frequencies are implied if: 1) the acoustic source is comprised of multiple frequencies, or 2) if the fluid dynamics involves nonlinear response to the driving pressure, which actively produces a multiple frequency response in the formation.

The contribution of a single fluid element to the NMR signal obtained in 210 depends on the cumulative position function $\vec{R}_\Sigma$:

$$\vec{R}_\Sigma(\vec{v}, \omega_a, \tau) = \int_\tau^{2\tau} \vec{R}(\vec{v}, \omega_a, t)dt - \int_0^\tau \vec{R}(\vec{v}, \omega_a, t)dt \tag{2}$$

where the cumulative position function $\vec{R}_\Sigma$ has units of distance-time; and the parameter τ is a time delay between the radio frequency pulses generated by the NMR tool 102.

The cumulative position function $\vec{R}_\Sigma$ enters the spin echo signal through the cumulative phase:

$$\Phi(2\tau) = \gamma \vec{G} \cdot \vec{R}_\Sigma(\vec{v}, \omega_a, \tau), \tag{3}$$

where $\vec{G}$ is a vector that specifies both the magnetic field gradient strength and direction in the volume 202ba, and γ is the nuclear gyromagnetic ratio.

The total component of the transverse magnetization following the Carr-Purcell-Meiborn-Gill pulse sequence is an average of the cumulative phase resulting from all fluid elements in the active volume of the gradient:

$$\frac{M(2\tau)}{M(0)} = \langle e^{i\Phi(2\tau)} \rangle \quad (4)$$

where the fluid elements are distinguished from each other by their respective pore velocities.

The average on the right hand side of (4) is expressed as:

$$\langle e^{i\Phi(2\tau)} \rangle = \langle e^{i\gamma \vec{G} \cdot \vec{R}_\Sigma(\vec{v},\omega_a,\tau)} \rangle = \int_{-\infty}^{\infty} e^{i\gamma \vec{G} \cdot \vec{R}_\Sigma(\vec{v},\omega_a,\tau)} P(\vec{v}) d\vec{v} \quad (5)$$

where $P(\vec{v})$ is the three dimensional velocity distribution function, and may implicitly depend upon $\omega_a$; and the number of fluid elements with a given velocity $\vec{v}$ is weighted by $P(\vec{v})$.

If the cumulative position $\vec{R}_\Sigma$ function depends linearly on the velocity in each of the principal spatial directions, then the amplitude of the spin echo signal is the Fourier transform of the velocity distribution function $P(\vec{v})$. Mathematically this situation is expressed as:

$$\vec{R}_E(\vec{v},\omega_a,\tau) = -\vec{\chi}(\omega_a,\tau) \cdot \vec{v},$$

where the coupling term, $\vec{\chi}(\omega_a, \tau)$, is tensoral in its most general form.

$$\langle e^{i\gamma \vec{G} \cdot \vec{R}_\Sigma(\vec{v},\omega_a,\tau)} \rangle = \int_{-\infty}^{\infty} e^{-i\gamma \vec{G} \cdot \vec{\chi} \cdot \vec{v}} P(\vec{v}) d\vec{v} = \hat{P}(\gamma \vec{G} \cdot \vec{\chi}) \quad (6)$$

The right hand side of (6) identifies the NMR signal as the Fourier transform of $P(\vec{v})$. Spin echo measurements, as expressed above in (4), are obtained for a variable set of $\vec{G}$ as depicted, for example in FIG. 3C. The Fourier amplitude for a given value of $\vec{G}$ is identified with the spin echo signal:

$$\hat{P}_{NMR}(\gamma \vec{G} \cdot \vec{\chi}) = \frac{M(2\tau, \vec{G})}{M(0)}. \quad (7)$$

In an exemplary embodiment, the spin echo signal from the Carr-Purcell-Meiborn-Gill pulse sequence is acquired over a range of $\vec{G}$ and/or a range of $\vec{\chi}(\omega_a, \tau)$, and the expansion of equation (6) in terms of statistical moments or cumulants of the velocity is implemented using known methods. This extraction of statistical moments may employ assumed relations amongst the statistical moments.

In an exemplary embodiment, the spin echo signal from the Carr-Purcell-Meiborn-Gill pulse sequence is acquired over a range of $\vec{G}$ and/or a range of $\vec{\chi}(\omega_a, \tau)$, and is used to construct the velocity distribution function $P(\vec{v})$ by Fourier inversion of (6):

$$P(\vec{v}) = \frac{1}{2\pi |\vec{\chi}|} \int_{-\infty}^{\infty} e^{i\gamma \vec{G} \cdot \vec{\chi} \cdot \vec{v}} \hat{P}_{NMR}(\gamma \vec{G} \cdot \vec{\chi}) d\vec{G} \cdot \vec{\chi} \quad (8)$$

Figure 4:
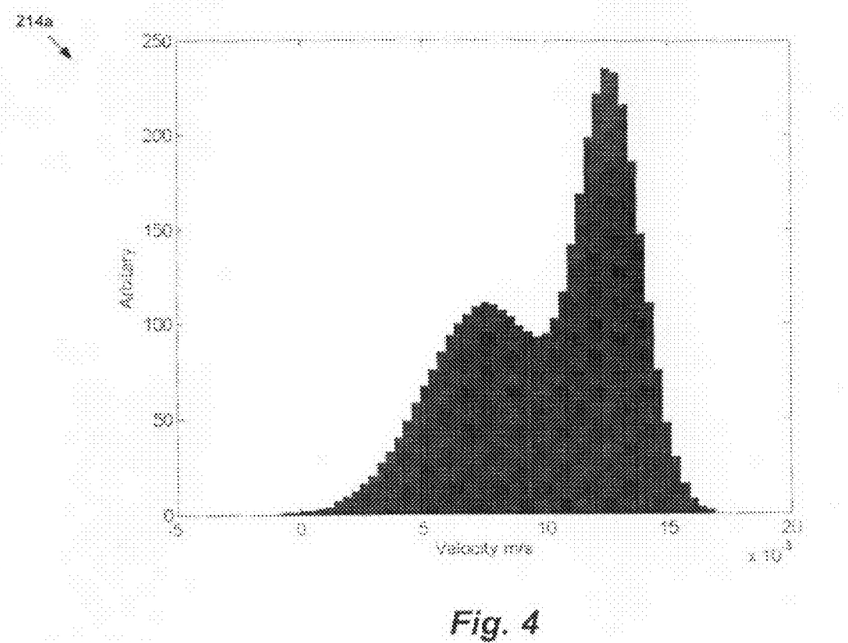
FIG. 4 is a graphical illustration of an exemplary embodiment of the determination of the pore fluid velocity distribution.

In an exemplary embodiment, as illustrated in FIG. 4, in 214, a pore fluid velocity distribution 214a is generated. In an exemplary embodiment, the velocity distribution is bi-modal.

In an exemplary embodiment, the fluid displacements are on the same scale or smaller than the average pore size, and $\vec{\chi}(\omega_a, \tau)$ is diagonal. In an exemplary embodiment, $\vec{\chi}(\omega_a, \tau)$ is given by the following equation:

$$\vec{\chi}(\omega_a, \tau) = -\frac{F(\omega_a, \tau, \phi_o)}{\omega_a^2} \cdot I,$$

where I is identity matrix and $F(\omega_a, \tau, \phi_o)$ is defined by the following equation:

$$F(\omega,\tau,\phi_0) = \cos\phi_0 - 2\cos(\omega\tau + \phi_0) + \cos(2\omega\tau + \phi_0),$$

where $\phi_0$ is the phase of the acoustic wave.

In an exemplary embodiment, $\phi_0$, is varied in order to adjust the value of $\vec{\chi}(\omega_a, \tau)$ for the inversion of (6), when the gradient is fixed. In an exemplary embodiment, $\tau$ is varied in order to adjust the value of $\vec{\chi}(\omega_a, \tau)$ for the inversion of (6), when the gradient is fixed.

In an exemplary embodiment, in 216, the average pore fluid velocity is then generated from the pore fluid velocity distribution 214a using conventional methods.

In an exemplary embodiment, in 218, if the pore fluid velocity distribution is not encompassed by the selected maximum field gradient and resolution, then 204, 206, 208, 210, 212, 214, and 216 are repeated. If, in 218, it is determined that the pore fluid velocity distribution is encompassed by the selected maximum field gradient and resolution, then the method 200 proceeds to 220.

In particular, the maximum gradient strength that is obtainable is one of the physical limitations in the NMR measurement that impacts the resolution of $P(\vec{v})$. Even simple measures of $P(\vec{v})$, like the mean squared deviation, are impacted by the maximum gradient strength. The equation (8) allows the gradient strength to be selected so that the $P(\vec{v})$ information content of the spin echo signal may be maximized.

In particular, the effect of finite gradient strength can be viewed in terms of a filter that acts on the fluid velocity distribution function. From the principles of Fourier analysis, a finite range on G is equivalent to the convolution of $P(v)$ with a sine function, $\text{Sinc}(a, v) = \text{Sin}(a \cdot v)/v$.

The effective distribution that is encoded in the spin echo signal is thereby equivalent to:

$$P_{G_m}(v, \omega_a) = \frac{1}{\pi} \int_{-\infty}^{\infty} \text{Sinc}(\gamma G_m \cdot \chi(\omega_a, \tau), y) \cdot P(v - y) dy \quad (9)$$

where $G_m$ is the maximum value of the gradient.

The distribution (9) is such that as $G_m \to \infty$, $P(v)$ is recovered from the convolution. The effective width of the sine function is $4.5/\gamma G \cdot \chi(\omega_a, \tau)$, so that any features in the velocity distribution function with finer structure than this width will not be encoded in the spin echo signal. For maximum resolution, both NMR parameters $\tau$ and G can be optimized within the physical constraints of the experimental setup. In other words, for any finite $G_m$ there is a distribution $P_{G_m}(v)$ that is wider than $P(v)$ and gives the same effective NMR signal when observations are restricted to the range finite range of $G < G_m$. The resolution by which the velocity distribution can be determined is set by $G_m$, and interpreted through equation (9). Thus, in selecting the maximum field gradient and resolution, the above teachings may be initially applied to 204 to select these parameters and later applied in 218 to determine if adjustments should be made.

In an exemplary embodiment, magnetic field inhomogeneity within pores are accounted for by inverting the following integral equation, or a mathematically equivalent form thereof:

$$P_{NMR}(v) = c \int_{-\infty}^{\infty} \frac{\mu_\varepsilon}{\mu_o - \mu_\varepsilon} P\left(\frac{v}{\mu_o - \mu_\varepsilon}\right) P(a\mu_\varepsilon^2) d\mu_\varepsilon,$$

where $\mu_o$ is the magnetic permeability of free space, and a and c are calibrated parameters.

In an exemplary embodiment, in 220, the pore size distribution is then calculated as follows:

$$P(\zeta) = 2\langle v \rangle \zeta \cdot P_{NMR}(\langle v \rangle \cdot \zeta^2) \quad (10)$$

The theoretical basis for the relationship in equation (10) above is as follows.

The fluid velocity in a capillary pore of radius r is given by the Poisseuille law:

$$v_r = -\frac{r^2}{8\eta} \cdot \frac{\Delta P}{l} \quad (11)$$

where $\Delta P$ is the pressure differential, l is the capillary length, and $\eta$ is the fluid viscosity.

Poisseuille flow gives rise to a Darcy law relation when dP/dz is identified with $\Delta P/l$. Performing the statistical average of (11) and comparing with the macroscopic Darcy law gives $k = \phi \langle r^2 \rangle / 8$ for the permeability, where $\phi$ is the porosity. The porosity is a structural assumption, because it is the density of capillaries.

The determination of k permits the pore size distribution function to be obtained from the velocity distribution function.

In particular, the average velocity can be used to eliminate the pressure differential in equation (11).

$$v_r = r^2 \cdot \frac{\langle v \rangle}{\langle r^2 \rangle} \quad (12)$$

Furthermore, all moments of velocity are determined with respect to the even moments of the pore radius distribution by (12). For example, $$\langle v^2 \rangle = \langle r^4 \rangle \cdot \left(\frac{\langle v \rangle}{\langle r^2 \rangle}\right)^2 \quad (13)$$

In addition, an immediate application of (12) is a structural interpretation of the ratio between $\sqrt{\langle \Delta v^2 \rangle}$ and $\langle v \rangle$:

$$\sqrt{\langle \Delta v^2 \rangle} = \beta \langle v \rangle, \quad (14)$$

with $$\beta = \sqrt{\frac{\langle r^4 \rangle}{\langle r^2 \rangle^2} - 1} = \frac{\sqrt{\langle r^4 \rangle - \langle r^2 \rangle^2}}{\langle r^2 \rangle}. \quad (15)$$

If the capillaries all posses a single pore radius, r, then $\beta = 0$, in agreement with $\langle \Delta v^2 \rangle = 0$.

The pore size radius distribution can be expressed in terms of the reduced radial quantity $\zeta = r / \sqrt{\langle r^2 \rangle}$ by equation (12), and is expressed as follows:

$$P(\zeta) = 2\langle v \rangle \zeta \cdot P_{NMR}(\langle v \rangle \cdot \zeta^2) \quad (16)$$

Figure 5:
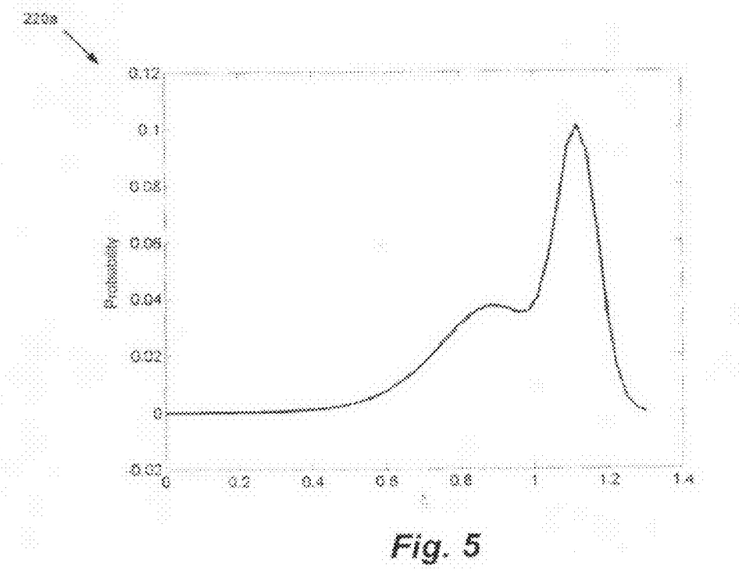
FIG. 5 is a graphical illustration of an exemplary embodiment of the determination of the pore size distribution.

In an exemplary embodiment, as illustrated in FIG. 5, in 220, a pore size distribution 220a is generated from the velocity distribution 214a in FIG. 4. In an exemplary embodiment, the pore size distribution 220a is bi-modal.

In an exemplary embodiment, in 222, the average pore size is then generated from the first moment of the velocity distribution, i.e., the average velocity, and/or the root mean squared velocity using known methods.

Figure 6:
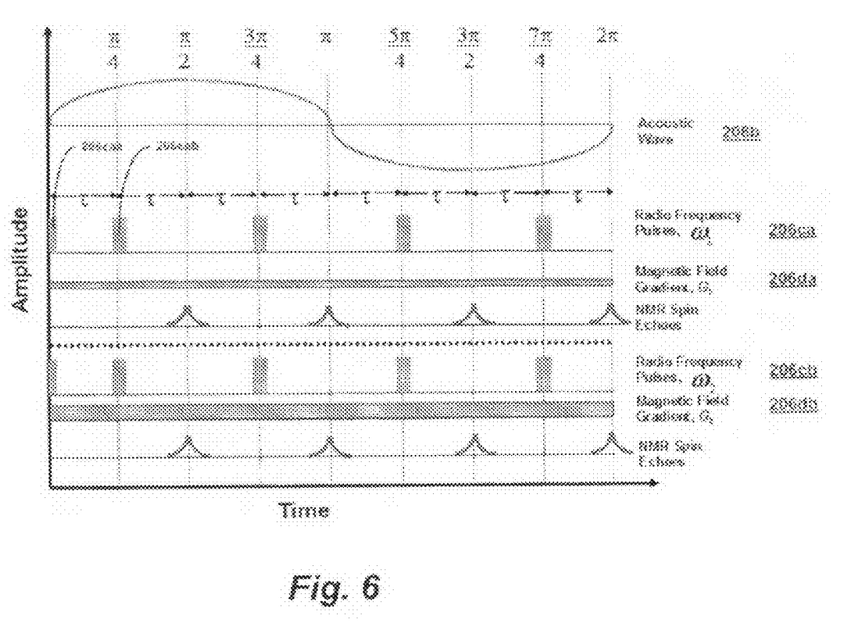
FIG. 6 is a graphical timing diagram illustrating and exemplary embodiment of the operation of the logging tool of FIG. 1.

In an exemplary embodiment, as illustrated in FIG. 6, in 206, the NMR tool 102 of the logging tool 100 is operated to transmit radio frequency pulses, 206ca and 206cb, into, and generate and magnetic field gradients, 206da and 206db, within, the formation 202b. In an exemplary embodiment, the phase and frequencies of the radio frequency pulses, 206ca and 206cb, are different and the magnitudes of the magnetic field gradients, 206da and 206db, are different. In an exemplary embodiment, the initial radio frequency pulses 206caa are spaced from the next radio frequency pulses 206cab by a time period $\tau$ and the next radio frequency pulses are spaced apart by a time period equal to $2\tau$. In an exemplary embodiment, the magnetic field gradients, 206da and 206db, are generated within different spatial volumes within the formation 202b.

In an exemplary embodiment, the operating frequencies of the radio frequency pulses and/or the magnetic field gradients may vary as a function of time and or spatial location within the formation 202b.

In an exemplary embodiment, the operating frequencies of the radio frequency pulses and/or the magnetic field gradients are unique.

In an exemplary embodiment, the spatial direction of the magnetic field gradients and the acoustic waves provided by the logging tool 100 are matched. For example, plane acoustic waves should be applied in the direction of an individual magnetic field gradient.

In an exemplary embodiment, during operation, the logging tool 100 provides a constant magnetic field gradient.

In an exemplary embodiment, in 206, 208, and 210, the magnetic field gradient is incrementally varied using a range of gradient strengths and spatial directions.

In an exemplary embodiment, the method 200 permits a direct measurement of fluid flow properties within a pore space within a subterranean formation.

In an exemplary embodiment, the method 200 induces a coherent displacement of fluidic materials within a pore space within a subterranean formation using acoustic energy. In an exemplary embodiment, the coherent displacement of the fluidic materials within the pore space may then be detected and characterized using magnetic field gradient NMR.

In an exemplary embodiment, during the operation of the method 200, acoustic and radio frequency waves are applied simultaneously in the presence of magnetic field gradients using the logging tool 100.

In an exemplary embodiment, during the operation of the method 200, the spin echo signals are timed with respect to the application of the acoustic waves and magnetic field gradients to the formation.

In an exemplary embodiment, during the operation of the method 200, the range of magnetic field gradient strengths and orientations is selected by the desired resolution of the velocity distribution.

In an exemplary embodiment, during the operation of the method 200, the pore size distribution is determined from the pore fluid velocity distribution.

A method of determining material properties within a portion of a subterranean formation has been described that includes injecting acoustic energy into the portion of the formation; generating a magnetic field gradient within the portion of the formation; injecting a radio frequency energy into the portion of the formation; measuring a spin echo signal from the portion of the formation; and processing the spin echo signal to determine one or more of the material properties of the portion of the subterranean formation; wherein the injecting of acoustic energy, the generating of the magnetic field, and the injecting of the radio frequency energy are performed simultaneously. In an exemplary embodiment, the magnetic field gradient is variable. In an exemplary embodiment, the magnetic field gradient varies with time. In an exemplary embodiment, the magnetic field gradient varies with spatial location. In an exemplary embodiment, the magnetic field gradient varies as a function of the desired resolution of the material properties. In an exemplary embodiment, the material properties comprise a pore fluid velocity distribution. In an exemplary embodiment, the method further comprises determining a pore size distribution from the pore fluid velocity distribution. In an exemplary embodiment, the material properties comprise an average pore fluid velocity. In an exemplary embodiment, the material properties comprise a pore size distribution. In an exemplary embodiment, the material properties comprise an average pore size. In an exemplary embodiment, the method further comprises performing a Fourier inversion or partial Fourier inversion of the spin echo signal to determine one or more of the material properties of the formation. In an exemplary embodiment, the acoustic energy comprises a periodic acoustic signal. In an exemplary embodiment, the periodic acoustic signal comprises a plurality of operating phases and frequencies. In an exemplary embodiment, the magnetic field gradient comprises a plurality of magnitudes and spatial distributions. In an exemplary embodiment, the radio frequency energy comprises a plurality of operating phases and frequencies. In an exemplary embodiment, a direction of the magnetic field gradient is substantially the same as a direction of propagation of the acoustic energy.

A method of determining material properties within a portion of a subterranean formation has been described that includes injecting a periodic acoustic signal into the portion of the formation; generating a magnetic field gradient within the portion of the formation; injecting radio frequency energy into the portion of the formation; measuring a spin echo signal from the portion of the formation; and processing the spin echo signal to determine one or more of the material properties of the portion of the subterranean formation by Fourier inversion of the spin echo signal; wherein the injecting of acoustic energy, the generating of the magnetic field, and the injecting of the radio frequency energy are performed simultaneously; wherein the material properties comprise a pore fluid velocity distribution and a pore size distribution; and wherein a direction of the magnetic field gradient is substantially the same as a direction of propagation of the acoustic energy.

A system for determining material properties within a portion of a subterranean formation has been described that includes means for injecting acoustic energy into the portion of the formation; means for generating a magnetic field gradient within the portion of the formation; means for injecting a radio frequency energy into the portion of the formation; means for measuring a spin echo signal from the portion of the formation; and means for processing the spin echo signal to determine one or more of the material properties of the portion of the subterranean formation; wherein the injecting of acoustic energy, the generating of the magnetic field, and the injecting of the radio frequency energy are performed simultaneously. In an exemplary embodiment, the magnetic field gradient is variable. In an exemplary embodiment, the magnetic field gradient varies with time. In an exemplary embodiment, the magnetic field gradient varies with spatial location. In an exemplary embodiment, the magnetic field gradient varies as a function of the desired resolution of the material properties. In an exemplary embodiment, the material properties comprise a pore fluid velocity distribution. In an exemplary embodiment, the system further comprises means for determining a pore size distribution from the pore fluid velocity distribution. In an exemplary embodiment, the material properties comprise an average pore fluid velocity. In an exemplary embodiment, the material properties comprise a pore size distribution. In an exemplary embodiment, the material properties comprise an average pore size. In an exemplary embodiment, the system further comprises means for performing a Fourier inversion of the spin echo signal to determine one or more of the material properties of the formation. In an exemplary embodiment, the acoustic energy comprises a periodic acoustic signal. In an exemplary embodiment, the periodic acoustic signal comprises a plurality of operating phases and frequencies. In an exemplary embodiment, the magnetic field gradient comprises a plurality of magnitudes and spatial distributions. In an exemplary embodiment, the radio frequency energy comprises a plurality of operating phases and frequencies. In an exemplary embodiment, a direction of the magnetic field gradient is substantially the same as a direction of propagation of the acoustic energy.

A system for determining material properties within a portion of a subterranean formation has been described that includes means for injecting a periodic acoustic signal into the portion of the formation; means for generating a magnetic field gradient within the portion of the formation; means for injecting radio frequency energy into the portion of the formation; means for measuring a spin echo signal from the portion of the formation; and means for processing the spin echo signal to determine one or more of the material properties of the portion of the subterranean formation by Fourier inversion of the spin echo signal; wherein the injecting of acoustic energy, the generating of the magnetic field, and the injecting of the radio frequency energy are performed simultaneously; wherein the material properties comprise a pore fluid velocity distribution and a pore size distribution; and wherein a direction of the magnetic field gradient is substantially the same as a direction of propagation of the acoustic energy.

A system for determining material properties within a portion of a subterranean formation has been described that includes a source of acoustic energy; a source of magnetic energy; a source of radio frequency energy; a sensor of spin echo signals; and a controller operably coupled to the source of acoustic energy, the source of magnetic energy, the source of radio frequency energy, and the sensor of spin echo signals; wherein the controller is adapted to measure spin echo signals, process spin echo signals to determine one or more of the material properties of the portion of the subterranean formation, and inject acoustic energy, magnetic energy, and radio frequency energy simultaneously into the formation using the source of acoustic energy, the source of magnetic energy, and the source of radio frequency energy. In an exemplary embodiment, the magnetic energy is variable. In an exemplary embodiment, the magnetic energy varies with time. In an exemplary embodiment, the magnetic energy varies with spatial location. In an exemplary embodiment, the magnetic energy varies as a function of the desired resolution of the material properties. In an exemplary embodiment, the material properties comprise a pore fluid velocity distribution. In an exemplary embodiment, the material properties comprise a pore size distribution. In an exemplary embodiment, the material properties comprise an average pore fluid velocity. In an exemplary embodiment, the material properties comprise a pore size distribution. In an exemplary embodiment, the material properties comprise an average pore size. In an exemplary embodiment, the controller is further adapted to perform a Fourier inversion of the spin echo signal to determine one or more of the material properties of the formation. In an exemplary embodiment, the acoustic energy comprises a periodic acoustic signal. In an exemplary embodiment, the periodic acoustic signal comprises a plurality of operating phases and frequencies. In an exemplary embodiment, the magnetic energy comprises a plurality of magnitudes and spatial distributions. In an exemplary embodiment, the radio frequency energy comprises a plurality of operating phases and frequencies. In an exemplary embodiment, the magnetic energy is substantially the same as a direction of propagation of the acoustic energy.

A system for determining material properties within a portion of a subterranean formation has been described that includes a source of acoustic energy; a source of magnetic energy; a source of radio frequency energy; a sensor of spin echo signals; and a controller operably coupled to the source of acoustic energy, the source of magnetic energy, the source of radio frequency energy, and the sensor of spin echo signals; wherein the controller is adapted to measure spin echo signals, process spin echo signals to determine one or more of the material properties of the portion of the subterranean formation, and inject acoustic energy, magnetic energy, and radio frequency energy simultaneously into the formation using the source of acoustic energy, the source of magnetic energy, and the source of radio frequency energy; wherein the material properties comprise a pore fluid velocity distribution and a pore size distribution; and wherein a direction of the magnetic energy is substantially the same as a direction of propagation of the acoustic energy.

It is understood that variations may be made in the foregoing without departing from the scope of the invention. For example, the teachings of the present illustrative embodiments may be used to provide a wellbore casing, a pipeline, or a structural support. Furthermore, the elements and teachings of the various illustrative embodiments may be combined in whole or in part in some or all of the illustrative embodiments. In addition, one or more of the elements and teachings of the various illustrative embodiments may be omitted, at least in part, and/or combined, at least in part, with one or more of the other elements and teachings of the various illustrative embodiments.

Although illustrative embodiments of the invention have been shown and described, a wide range of modification, changes and substitution is contemplated in the foregoing disclosure. In some instances, some features of the present invention may be employed without a corresponding use of the other features. Accordingly, it is appropriate that the appended claims be construed broadly and in a manner consistent with the scope of the invention.

What is claimed is:

1. A method of determining material properties within a portion of a fluid-containing porous medium, the porous medium being part of a subterranean formation, the method comprising:
   a) injecting acoustic energy into the portion of the porous medium;
   b) generating a magnetic field gradient within the portion of the porous medium;
   c) injecting a radio frequency energy into the portion of the porous medium;
   wherein the acoustic energy, the magnetic field gradient, and radio frequency energy have a predetermined relationship in time;
   d) measuring an NMR signal from the portion of the porous medium;
   e) repeating a), b), c), and d) for one or more different values of the magnetic field gradient;
   f) processing the measured NMR signals to determine at least one material property of the porous medium, wherein the at least one material property comprises a pore fluid velocity distribution; and
   g) determining a relative pore size distribution from the pore fluid velocity distribution.

2. The method of claim 1, wherein the porous medium is a sample selected from the subterranean formation.

3. The method of claim 1, wherein a), b), and c) are performed with a logging tool positioned within a wellbore of the part of the subterranean formation.

4. The method of claim 1, wherein the measured NMR signal comprises a spin echo.

5. The method of claim 4, wherein the acoustic energy is injected as a periodic wave and the radio frequency energy is injected in periodic series of pulses, and the predetermined relationship in time comprises beginning the acoustic and radio frequency energy injections simultaneously with periods chosen to maintain a predetermined phase relationship between the acoustic and radio frequency energy injections and the measured NMR spin echoes.

6. The method of claim 5, wherein the acoustic wave period is an integer multiple of the radio frequency energy pulse period.

7. The method of claim 1, wherein the magnetic field gradient is variable.

8. The method of claim 1, wherein the magnetic field gradient varies with time.

9. The method of claim 1, wherein the magnetic field gradient varies with spatial location.

10. The method of claim 1, wherein the magnetic field gradient varies as a function of the desired resolution of the material properties.

11. The method of claim 1, further comprising:
   determining an absolute pore size distribution from the pore fluid velocity distribution and a mean pore size that is determined from the relative pore size distribution.

12. The method of claim 1, wherein the acoustic energy comprises a periodic acoustic signal.

13. The method of claim 12, wherein the periodic acoustic signal comprises a plurality of operating phases and frequencies.

14. The method of claim 1, wherein the magnetic field gradient comprises a plurality of operating frequencies.

15. The method of claim 1, wherein the radio frequency energy comprises a plurality of operating phases and frequencies.

16. The method of claim 1, wherein a direction of the magnetic field gradient is substantially the same as a direction of propagation of the acoustic energy.

17. The method of claim 1 wherein a spatial direction of the magnetic field gradient is not the same as a direction of a propagating wave of the acoustic energy.

18. The method of claim 1, wherein the predetermined relationship in time is that the acoustic energy, the magnetic field gradient, and radio frequency energy occur simultaneously at each measurement location.

19. The method of claim 1, further comprising using the at least one material property to assess the economics of the subterranean formation or for planning development of hydrocarbon production from the subterranean formation.

20. The method of claim 1, wherein the at least one material property further comprises one or more of fluid displacement, fluid velocity, and an average pore fluid velocity.

21. The method of claim 1, wherein the acoustic energy is injected as a periodic wave and the radio frequency energy is injected in periodic series of pulses, and the predetermined relationship in time comprises maintaining a selected temporal relationship between the radio frequency pulses and the acoustic energy wave.

22. The method of claim 21, wherein the measuring an NMR signal is repeated for different values of the selected temporal relationship between the radio frequency pulses and the acoustic energy wave.

23. A method of determining material properties within a portion of a fluid-containing porous medium, the porous medium being part of a subterranean formation, the method comprising:
   a) injecting acoustic energy into the portion of the porous medium;
   b) generating a magnetic field gradient within the portion of the porous medium;
   c) injecting a radio frequency energy into the portion of the porous medium;
   wherein the acoustic energy, the magnetic field gradient, and radio frequency energy have a predetermined relationship in time;
   d) measuring an NMR signal from the portion of the porous medium;
   e) repeating a), b), c), and d) for one or more different values of the magnetic field gradient;
   f) processing the measured NMR signals to determine at least one material property of the porous medium, wherein the material property comprises one or more properties selected from the group consisting of fluid displacement, fluid velocity, a pore fluid velocity distribution, and an average pore fluid velocity; and
   g) performing a Fourier inversion or a partial Fourier inversion, on the measured NMR signal, to determine one or more of the material properties of the formation.

24. Method of claim 23, wherein the at least one material property includes the pore fluid velocity distribution, and the Fourier inversion on the measured NMR signal utilizes a relationship whereby spin echo amplitude in the measured NMR signal is the Fourier transform of the pore fluid velocity distribution.

25. A method of determining material properties within a portion of a fluid-containing porous medium, the porous medium being part of a subterranean formation, the method comprising:
   a) injecting acoustic energy into the portion of the porous medium;
   b) generating a magnetic field gradient within the portion of the porous medium;
   c) injecting a radio frequency energy into the portion of the porous medium;
   wherein the acoustic energy, the magnetic field gradient, and radio frequency energy have a predetermined relationship in time;
   d) measuring an NMR signal from the portion of the porous medium;
   e) repeating a), b), c), and d) for one or more different values of the magnetic field gradient; and
   f) determining statistical moments of the measured NMR signals to determine at least one material property of the porous medium, wherein the material property comprises one or more properties selected from the group consisting of fluid displacement, fluid velocity, a pore fluid velocity distribution, and an average pore fluid velocity.

26. The method of claim 25, wherein the one or more material properties of the formation are determined using correlations among the statistical moments.

27. A method of determining material properties within a portion of a fluid-containing porous medium, the porous medium being part of a subterranean formation, the method comprising:
   a) injecting acoustic energy into the portion of the porous medium;
   b) generating a magnetic field gradient within the portion of the porous medium;
   c) injecting a radio frequency energy into the portion of the porous medium;
   wherein the acoustic energy, the magnetic field gradient, and radio frequency energy have a predetermined relationship in time;
   d) measuring an NMR signal from the portion of the porous medium;
   e) repeating a), b), c), and d) for one or more different values of the magnetic field gradient; and
   f) determining cumulants of the measured NMR signals to determine at least one material property of the porous medium, wherein the material property comprises one or more properties selected from the group consisting of fluid displacement, fluid velocity, a pore fluid velocity distribution, and an average pore fluid velocity.

28. A method of producing hydrocarbons from a subterranean formation, comprising:
   a) injecting acoustic energy into the portion of the formation;
   b) generating a magnetic field gradient within the portion of the formation;
   c) injecting a radio frequency energy into the portion of the formation;
   wherein the acoustic energy, the magnetic field gradient, and radio frequency energy have a predetermined relationship in time;
   d) measuring an NMR signal from the portion of the formation;
   e) repeating a), b), c), and d) for one or more different values of the magnetic field gradient;
   f) processing the measured NMR signals to determine one or more of the material properties of the subterranean formation, wherein the material property comprises a pore fluid velocity distribution;
   g) determining a relative pore size distribution from the pore fluid velocity distribution; and
   h) using the determined relative pore size distribution in producing hydrocarbons from the subterranean formation.

29. A method of producing hydrocarbons from a subterranean formation, comprising:
   a) injecting acoustic energy into the portion of the formation;
   b) generating a magnetic field gradient within the portion of the formation;
   c) injecting a radio frequency energy into the portion of the formation;
   wherein the acoustic energy, the magnetic field gradient, and radio frequency energy have a predetermined relationship in time;

d) measuring an NMR signal from the portion of the formation;
e) repeating a), b), c), and d) for one or more different values of the magnetic field gradient;
f) processing the measured NMR signals to determine one or more of the material properties of the subterranean formation, wherein the material property comprises one or more properties selected from the group consisting of fluid displacement, fluid velocity, a pore fluid velocity distribution, and an average pore fluid velocity;
g) determining statistical moments from the measured NMR signal; and
h) using correlations among the moments in determining one or more of the material properties of the formation.

* * * * *